United States Patent
Perry

Patent Number: 6,099,564
Date of Patent: Aug. 8, 2000

[54] SELF-TAPPING PEGS FOR ORBITAL IMPLANTS

[76] Inventor: Arthur C. Perry, 16418 La Via Feliz, Rancho Santa Fe, Calif. 92067-1102

[21] Appl. No.: 08/886,600

[22] Filed: Jul. 1, 1997

Related U.S. Application Data

[63] Continuation-in-part of application No. 08/853,647, May 9, 1997.

[51] Int. Cl.[7] .......................................................... A61F 2/14
[52] U.S. Cl. .......................................... 623/4.1; 623/11.11
[58] Field of Search ..................................... 623/4, 11, 16

[56] References Cited

U.S. PATENT DOCUMENTS

| | | | |
|---|---|---|---|
| 2,617,994 | 11/1952 | Noelle | 623/4 |
| 2,810,134 | 10/1957 | Radin | 623/4 |
| 4,976,731 | 12/1990 | Perry . | |
| 5,026,392 | 6/1991 | Gordon . | |
| 5,466,259 | 11/1995 | Durette | 623/4 |

OTHER PUBLICATIONS

The Journal of the American Society of Ocularists 1992 23rd Annual Edition. pp. 48 and 49 by Kolberg Applegate.

*Primary Examiner*—Mickey Yu
*Assistant Examiner*—Choon P. Koh
*Attorney, Agent, or Firm*—Henri J.A. Charmasson; John D. Buchaca

[57] ABSTRACT

An orbital implant motility peg comprising a means for placement in vivo in a non-drilled integrated orbital implant. The peg or portions thereof can be fabricated from titanium, a titanium alloy, stainless steel, a CoCr alloy, alumina, platinum or tantalum. The means for placement can comprise an external surface of the peg which comprises threads, to facilitate screwing into the implant, and/or a slot capable of receiving a screwdriver tip, a receptacle capable of receiving a Phillips screwdriver tip, a polygonal surface capable of being held by a wrench, or a receptacle capable of being engaged by an Allen wrench.

11 Claims, 3 Drawing Sheets

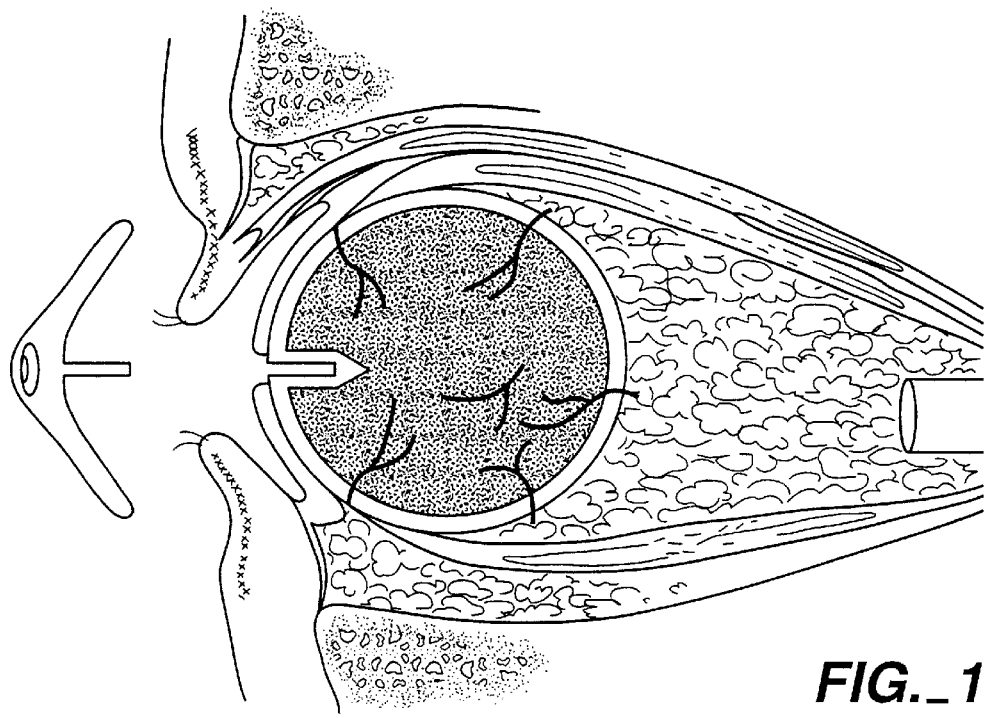
FIG._1
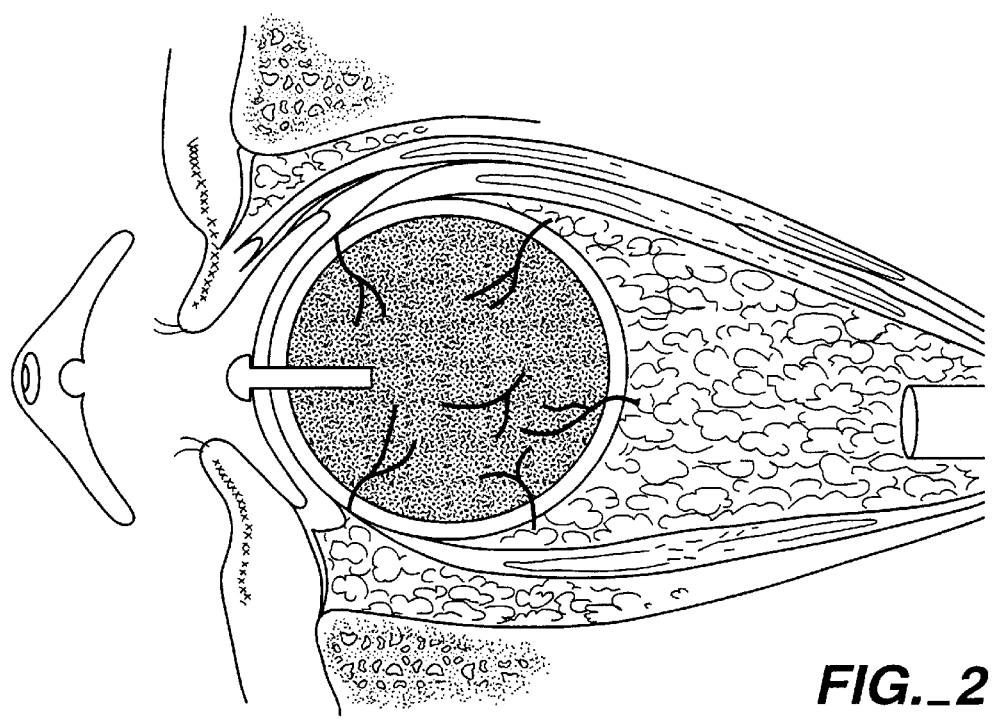
FIG._2

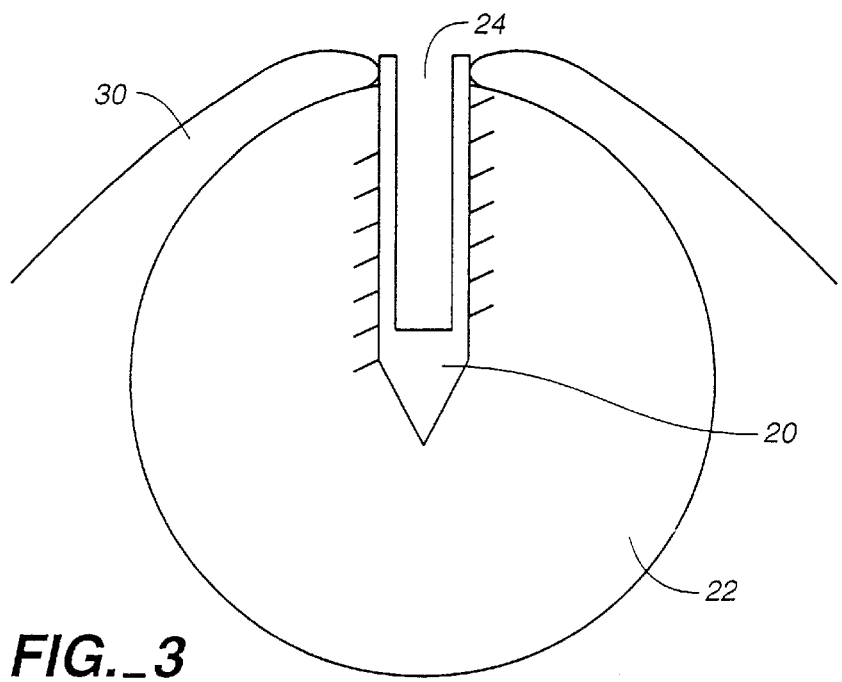
FIG._3
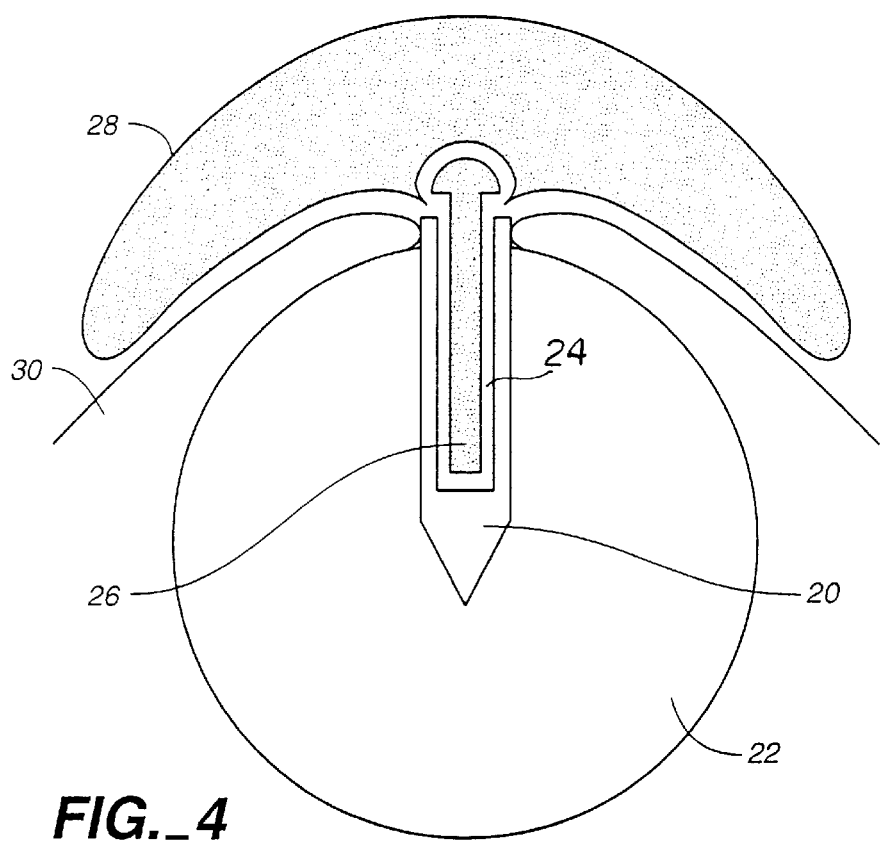
FIG._4

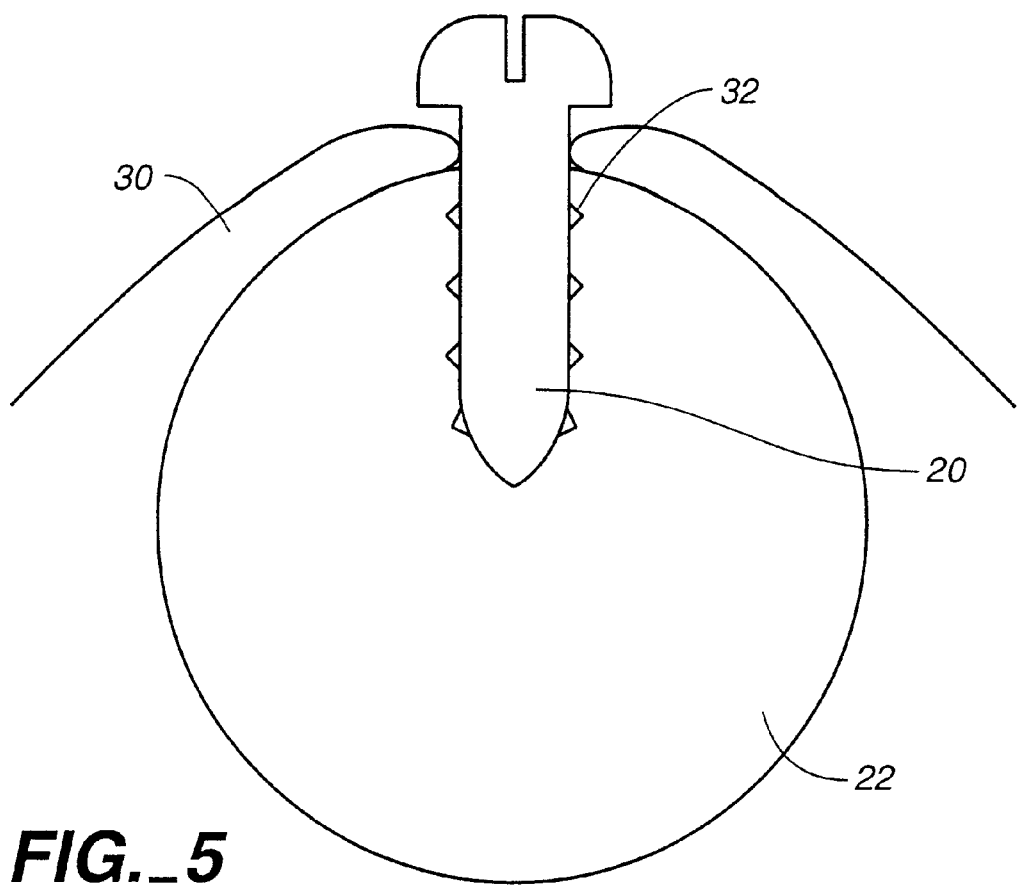
FIG._5

SELF-TAPPING PEGS FOR ORBITAL IMPLANTS

PRIOR APPLICATIONS

This application is a continuation-in-Part of the U.S. application Ser. No. 08/853,647 entitled "Pegs for Orbital Implants" filed May 9, 1997 in the name of Arthur C. Perry, from which priority is claimed and which is fully incorporated by reference herein.

FIELD OF THE INVENTION

This invention relates to prosthetic organs. More particularly, it relates to a self-tapping "peg" for attaching an artificial eye to an integrated orbital implant.

BACKGROUND ART

Enucleation or evisceration of the eye is performed because of disease or trauma that makes the removal of the eye, or the intraocular contents of the eye, necessary. Following either such procedure, the patient normally desires use of an artificial eye to restore a more normal appearance. The artificial eye is generally a large contact lens shaped object, which contains components that create the impression of the external aspects of an eye, i.e., an iris, pupil and sclera. To satisfactorily fit an artificial eye into the orbital socket, an orbital implant must be placed within the orbit to replace the volume that was lost when the eye or its contents was removed.

The use of an orbital implant and the subsequent fitting of the artificial eye confer more than a cosmetic benefit. They help maintain the normal structure of the eyelids and eyebrows; they aid in normal tear drainage; and, when used in children, they help stimulate normal growth of the orbital bones.

Even though an artificial eye can be made which has a very realistic appearance, prior to the present invention such artificial eyes have failed to track in conjunction with the normal eye because there was no coupling between the artificial eye and the orbital implant. The artificial eye drifted within the socket and did not track with the normal eye. This lack of tracking was quite apparent and disconcerting to even a casual observer, creating a sense of self-consciousness on the part of the patient.

Consequent to the shortcomings of traditional implants, efforts have been made to attach the eye muscles to the implant, and then to attach the artificial eye to the implant. This provided adequate tracking of the artificial eye. The success was short-lived because, in a brief period of time, the implant was extruded from the orbit. Implant extrusion occurred because the fixing of the artificial eye to the implant material exposed the implant to the outside environment. This permitted infectious agents such as bacteria to enter, and the implant became chronically infected. Exposure of these implants to the external environment was necessary to produce an attachment between the implant and the artificial eye.

A wide variety of materials have been used for orbital implants, such as ivory spheres, gold globes, silk, catgut, acrylic plastics or silicones, human bone (G. C. Sood al *International Surgery*, (1970) Vol. 54, No. 1, p. 1); and antigen-free cancellous calf bone, so called "Kiel Bone," (A. C. B. Molteno, et al., *Brit. J. Ophthal.*, (1973) Vol. 57, p. 615 and A. C. B. Molteno, *Trans: of the Ophthal. Soc. New Zealand* (1980) Vol. 32, p. 36. These materials did not provide for significant integration of tissue and vascularization of the implant. As described in U.S. Pat. No. 4,976,731, these materials were disadvantageous in that the patient risked chronic infection as a result of subsequent procedures necessary to connect the implant to the artificial eye so that the artificial eye would track with the patient's contralateral eye. Also, the weight of the artificial eye was not supported by the implant. This lack of support puts pressure on the lower lid causing lower lid sagging.

A porous orbital implant overcomes these problems. One type of porous orbital implant is described in U.S. Pat. No. 4,976,731. In the 4,976,731 patent, the use and preparation of a porous orbital implant comprising hydroxyapatite is described. The use of porous implants allowed integration of the implant with fibrovascular tissue. Integrated implants provided advantages over other implant materials particularly because integration of the patient's own tissue allowed coupling of the implant to the artificial eye, and increased the long-term stability of both the artificial eye and the implant.

As disclosed in copending applications, e.g., Ser. Nos. 08/241,960 filed May 12, 1994; and, 08/660,095 filed Jun. 6, 1996, in order to couple an artificial eye to an integrated implant, the implant must generally be drilled (i.e., "tapped") so that a peg capable of connecting the implant to the artificial eye can be placed. It was necessary to pre-tap the integrated implants because the material used for the pegs lacked the strength to be inserted into the implant without pre-tapping. Pre-tapping, however, can sometimes be disadvantageous in that the surgeon must acquire additional equipment, e.g., a motorized drill. Furthermore, the use of a drill on delicate orbital tissue can lead to tissue trauma.

The need for self-tapping integrated orbital implant pegs is also related to the need to find more reliable implant materials to replace broken or deteriorating parts of the human body. Implant materials are needed in modern surgery and dentistry, such as metals and alloys, which are extremely chemically inert and which have adequate mechanical strength.

The first metal alloy developed specifically for human implant use was "vanadium steel", which was used to manufacture bone fracture plates (Sherman plates) and screws. Most metals such as iron (Fe), chromium (Cr), cobalt (Co), nickel (Ni), titanium (Ti), tantalum (Ta), molybdenum (Mo), and tungsten (W) used to make alloys for use in implants can be tolerated by the body in minute amounts. Sometimes those metallic elements, in naturally occurring forms, are essential in cell functions (Fe) or synthesis of vitamin $B_{12}$ (Co) but cannot be tolerated in large amounts in the body. The biocompatibility of a metallic implant is of considerable concern because these implants can corrode in an in vivo environment. The consequence of corrosion are the disintegration of the implant material per se, which will weaken the implant, and the potentially harmful effect of corrosion products which escape into the surrounding tissue.

Metals and alloys in common use include stainless steels, Co—Ni—Cr alloy, cast and wrought Co—Cr—Mo alloy, commercially pure titanium, Ti-6A1-4V alloy and other titanium alloys. Biomaterial development is proceeding in the area of polymers, ceramics, combination materials such as zirconia-hydroxyapatite, and with aluminum oxide (alumina) which can be made with various degrees of porosity and strength. Key objectives with the development of these materials, as with metals and metal alloys, is biocompatability and strength.

Presently, commercially pure titanium is a material of choice for many implants, because of its biocompatibility resulting in no allergic reaction with the surrounding tissue and also no thrombotic reaction with the blood of the human body.

Stainless Steels

The first stainless steel utilized for implant fabrication was 18–8 (type 302 in modern classification), which is stronger and more resistant to corrosion than the vanadium steel. Vanadium steel is no longer used in implants, since its corrosion resistance is inadequate in vivo. Later 18–8sMo stainless steel, which contains a small percentage of molybdenum to improve the corrosion resistance in salt water, was introduced. This alloy became known as type 316 stainless steel. In the 1950s, the carbon content of 316 stainless steel was reduced from 0.08% (all are weight percentages unless specified) to 0.03% maximum for better corrosion resistance to chloride solution and became known as type 316L stainless steel. The minimum effective concentration of chromium is 11% to impart corrosion resistance in stainless steels. Chromium is a reactive element, but it and its alloys can be passivated to give excellent corrosion resistance.

CoCr Alloys

There are basically two types of cobalt-chromium alloys; one is the CoCrMo alloy which is usually used to cast a product and the other is CoNiCrMo alloy, which is usually wrought by (hot) forging. The two basic elements of the CoCr alloys form a solid solution of up to 65% Co. The molybdenum is added to produce finer grains which results in higher strengths after casting or forging.

The castable CoCrMo alloy has been used for many decades in dentistry and, recently, in making artificial joints. The wrought CoNiCrMo alloy is a relative newcomer now used for making the stems of prostheses of heavily loaded joints such as the knee and hip.

The CoNiCrMo alloy, originally called MP35N (Standard Pressed Steel Co.), contains approximately 35% Co and Ni each. The alloy is highly corrosion resistant to seawater (containing chloride ions) under stress. Cold working can increase the strength of the alloy considerably. However, there is considerable difficulty in cold working this alloy, especially when making large devices such as hip joint stems. Only hot-forging can be used to fabricate a large implant with the alloy.

The mechanical properties required for CoCr alloys are, as with other alloys, that increased strength is accompanied by decreased ductility. Both the cast and wrought CoCr alloys have excellent corrosion resistance.

Ti and Its Alloys

Titanium was discovered in 1794 and is the ninth most common element in the earth's crust, occurring as rutile, TiO2. Extraction of titanium in amounts that were large enough for commercialization came about with the developments of the Kroll process in 1936. Titanium has a high strength-to-weight ratio that makes it attractive for many applications. Attempts to use titanium for implant fabrication date from the late 1930s. It was found that titanium was tolerated in cat femurs, as was stainless steel and Vitallium (CoCrMo alloy). Commercially pure titanium and the common titanium alloy, Ti-6A1-4V, have been in use as implant materials for a shorter time compared with stainless steel and cast or wrought cobalt based alloys.

Titanium's lightness (4.5 g/cm$^3$ compared to 7.9 g/cm$^3$ for 316 stainless steel, 8.3 g/cm$^3$ for cast CoCrMo, and 9.2 g/cm$^3$ for wrought CoNiCrMo alloys) and good mechanochemical properties are salient features for implant application. Titanium alloys are prominent as dental and orthopedic implant materials because of their high strength-to-weight ratio, lower elastic modulus, excellent corrosion resistance and apparent biocompatibility.

Titanium and its alloys are used in orthopedic surgery as implants in the shape of wires, nails, plates and screws for the fixation and stabilization of fractures or in the form of artificial joints for the replacement of joints of the human body. Some implants are used for short time durations in the human body, whereas others remain in place for decades. To avoid a reoperation caused by the implant material, the material must meet certain chemical and mechanical requirements. Chemical requirements include high biocompatibility without altering the environment of the surrounding tissue even under deformation and sterilization. Mechanical property requirements relate to specific strength, modulus, fatigue, creep and fracture toughness which, in turn relate to microstructures.

To attain higher strength than commercially pure titanium, alloying elements are added. Alloy design criteria are not based only on alloying elements contribution to strength, but on the biocompatibility of the resulting alloy. Alloying additions and thermomechanical processing dictate the microstructure of the implant material, and control of microstructure is a means to attain desirable properties.

As the impurity content of commercially pure titanium becomes higher, there is increased strength and reduced ductility. The strength of the material varies from a value much lower than that of 316 stainless steel or the CoCr alloys, to a value about equal to that of annealed 316 stainless steel or the cast CoCrMo alloy. However, when compared by specific strength (strength per density), the titanium alloys excel relative to other implant materials. Titanium, nevertheless, has poor shear strength, making it less desirable for bone screws, plates, and similar applications. Titanium also tends to gall or seize when in sliding contact with itself or another metal.

Based on structures that can be produced by alloying, titanium alloys are grouped as alpha, alpha-beta and beta alloys. Alpha titanium and alpha-beta alloys have been used for dental and orthopedic purposes. Beta titanium alloys are being considered as candidate materials for implant applications because of their ease of formability, increased strength and lower elastic modulus, in spite of increased cost. Studies show the presence of the omega phase in the beta alloy, Ti-15Mo-2.8Nb, in the unaged condition. Comparison of corrosion behavior of this alloy with the alloy Ti-6A1-4V shows the two alloys have comparable corrosion resistance in simulated physiological solution.

Surface treatment variations such as porous coatings, ion implantation and oxidation are made to the titanium implant devices for various reasons; all directed to improving performance and biocompatibility. The use of "new" alloys and associated heat treatments and surface variations may result in changes in the mechanical and chemical behavior that ultimately affect the strength, durability and biocompatibility of the implant.

The physical properties of titanium alloys are affected by several parameters. Alloying elements and thermomechanical processing including shaping and sizing of the implants, affect the various aspects of mechanical properties in different ways. In general, increasing the strength by alloying or by thermomechanical processing decreases the fracture toughness of the material. Increasing the grain size is detrimental to fatigue behavior; however, creep resistance is increased. Cold working and hot working at relatively low temperatures develop a texture that, in turn, makes the mechanical behavior of the metal non-isotropic. Non-isotropic mechanical behavior may be useful in applications where directional properties are needed for improving reliability of the implant material.

As set forth above, integrated orbital implants allow vascularization of the implant itself. As a result of the shortcomings of prior implant pegs, there exists a need for means for attaching an artificial eye to an implant without the need for pre-drilling the implant.

DISCLOSURE OF THE INVENTION

Disclosed is a self-tapping orbital implant motility peg. In preferred embodiments the peg comprises a means for removable attachment to an artificial eye or a component of an articulation at a distal end thereof. The peg can be configured to permit rotation of the peg itself or an artificial eye associated therewith, relative to a longitudinal axis of the peg; the rotation can occur during or following insertion of the peg into an orbital implant. Methods of using such pegs are disclosed.

Disclosed is a self-tapping integrated orbital implant motility peg. Disclosed is an orbital implant motility peg comprising a means for placement in vivo in a non-drilled integrated orbital implant. The peg can comprise a peg portion fabricated from titanium, a titanium alloy, stainless steel, alumina, a CoCr alloy, platinum or tantalum. The means for placement can comprise an external surface of the peg that is threaded, to facilitate screwing of the peg into the implant. The means for placement can comprise a slot capable of receiving a screwdriver tip, a receptacle capable of receiving a Phillips screwdriver tip, a polygonal surface capable of being held by a wrench, or a receptacle capable of being engaged by an Allen wrench.

Disclosed is a sheath-like embodiment of the self-tapping peg. The sheath-like embodiment is capable of containing a stint in a peg lumen; the stint is for attaching the peg to an artificial eye. The stint can comprise a means for removable attachment to an artificial eye, or it can be permanently attached to an artificial eye. The means for removable attachment from the stint can comprise a convex surface capable of articulating with a concave surface on the artificial eye. The means for removable attachment of the stint can comprise a ball or socket of a ball-and-socket articulation. The stint can comprise circumferential indentations regularly spaced along a longitudinal axis thereof, whereby a length of the stint can be shortened by breaking at any one of the circumferential indentations by bending the stint. The circumferential indentations of the stint can be regularly spaced at about every 3 mm. The stint can be fabricated of a bendable material, whereby said stint material retains an amended shape following bending; the bendable material can be stainless steel.

Disclosed is a method to facilitate coupling of an artificial eye to an integrated orbital implant, said method comprising: surgically placing an intact integrated orbital implant into the socket of a patient who has had an ocular enucleation or evisceration; waiting a time period sufficient for fibrovascular tissue to grow into the implant; providing a self-tapping motility peg that is attached to or is attachable to an artificial eye; and, placing the peg into the intact integrated orbital implant.

Set forth below are the preferred embodiments. These embodiments are illustrative, and are not intended to be limitations to the appended claims.

DESCRIPTION OF FIGURES

FIG. 1 is a schematic representation of an implant showing a sheath-like embodiment of the self-tapping implant peg and stint directly attached to an artificial eye.

FIG. 2 is a schematic representation of an implant having a rod-like self-tapping peg placed therein, which peg has a rounded head capable of making a "ball-and-socket" coupling with a corresponding recess on an artificial eye.

FIG. 3 is a representation of a sheath-like embodiment of a self-tapping peg placed in an integrated orbital implant.

FIG. 4 depicts a sheath-like embodiment of the peg with a stint placed therein, and that the stint is attached to an artificial eye by a ball-and-socket joint.

FIG. 5 depicts a rod-like embodiment of the self-tapping peg.

MODES FOR CARRYING OUT INVENTION

Definitions

As used herein, orbital implant is synonymous with ocular implant.

The term "integrated" is used herein to denote those implants into which the orbital tissue of the recipient is capable of penetrating.

The terms "prosthesis" and "prosthetic complex" refer to an artificial eye and a peg; the peg can either be directly attached or attachable to the artificial eye.

An "anophthalmic socket" is a socket that lacks an eye. The socket may lack an eye, e.g.: congenitally, due to trauma, due to an enucleation, or due to an evisceration.

The term "tapped" often indicates that an implant is drilled so that a peg capable of connecting the implant to the artificial eye can be placed in the drilled hole. A "self-tapping" peg does not require pre-drilling before the peg can be placed in an implant. Optionally, however, a surgeon could pre-drill an implant before placing a self-tapping peg.

The term "intact implant" is intended to refer to an implant that is nondrilled.

Orbital Implants and Prosthetic Complexes

The present invention concerns integrated orbital implants. As set forth above, the term "integrated" herein denotes those implants into which the recipient's own tissue will penetrate as the socket surrounding the implant heals. Although non-integrated implants are less preferred, the peg of the invention may be used therewith to the extent the patient's clinical context permits, and one skilled in the art will recognize the extent to which the structures, compositions and methods described herein are applicable thereto.

Low density, porous hydroxyapatite of the kind obtained from coral or by synthetic means is a preferred material for the integrated orbital implant. Implants made of low density, porous hydroxyapatite are available from Integrated Orbital Implants, Inc., San Diego, Calif. A less preferred material is granular high density hydroxyapatite, such as that used as bone grafting material. For low density hydroxyapatite, spheres were machined to appropriate sizes to be used as implants from a larger block of porous hydroxyapatite. Alternatively, integrated implants can be fabricated from porous polyethylene, or other biocompatible porous materials.

The hydroxyapatite implants were sterilized, preferably by autoclaving, prior to being used in the surgical procedures described herein.

As noted above, orbital implants may be used in eviscerations, where the contents of the eyeball are removed; in this context a coating or wrapping around the implant was typically provided by the patient's own scleral sac which was sewn closed around the implant. For enucleation, where the entire eyeball is removed (after severing it from the eye muscles and the optic nerve); the implant may be placed inside coating material which may be sutured closed, or the implant may be dipped in coating material.

Integrated implants have also been useful for replacing a previous orbital implant. Such "secondary" replacement is particularly important as some patients may desire to replace their original non-integrated implant with an integrated orbital implant so as to achieve more natural movement, and more natural eye position. Secondary replacement may also be required if the previous implant has migrated, has become exposed, or has been extruded. For secondary implant replacement, if desired, the implant can be coated, e.g., it can be placed inside coating material which may be closed via suturing (if appropriate), or the implant may be dipped in coating material prior to use. In the above surgical procedures, the implant or, if coated, the coated implant may then be sutured to the patient's extraocular muscles of the orbit.

Generally, after implantation of an integrated orbital implant, the socket was allowed to heal for approximately six months. During the healing process, fibrovascular tissue penetrates the porous structure of the implant as any coating material is gradually absorbed or penetrated.

After sufficient in-growth of fibrovascular tissue, the implant a "peg" can be placed which is directly or indirectly coupled to an artificial eye. U.S. Pat. No. 4,976,731, issued to the present inventor herein, sets forth two embodiments for connecting an orbital implant to an artificial eye. In one embodiment, illustrated in FIGS. 1 and 4, the artificial eye is permanently fitted with a stint which then fits into a hole in a sheath-like embodiment of a self-taping peg, thus coupling the implant with the artificial eye. In alternative embodiments, a rod-like embodiment of the self-tapping peg (FIGS. 2 and 5), or a protruding stint placed into a hole of a sheath-like peg, has a rounded surface that mates with a corresponding surface on the back of an artificial eye, thereby coupling the artificial eye to the integrated implant.

In accordance with the novel pegs of the present invention, it is no longer necessary for a hole to be drilled in the integrated implant. One skilled in the art will recognize other means to attach the artificial eye to the implant which has integrated.

Integrated implants have been very satisfactory from the patient's point of view. The implant resisted extrusion from the orbit. Instead, it became an integral part of the orbital structure because of the integration of the fibrovascular tissue into the porous material. Being fixed to the eye muscles, the implant was capable of tracking with the normal eye. When an artificial eye was fixed to the implant to complete the prosthesis, a very satisfactory, natural appearance results.

To date, over 35,000 patients have had porous hydroxyapatite orbital implants implanted into their orbits. In patients with vascularized implants, there have been no chronic infections or extrusions of the implant, where these patients have been followed up to 11 years.

Connections Between a Peg and an Artificial Eye

For example, where a peg was placed into an implant, and the artificial eye comprised a recess to receive the peg, the distal end of the peg could be essentially round in a cross-section taken relative to the longitudinal axis of the peg, so that there is rotation of the artificial eye around a longitudinal axis of the peg. As appreciated by one of ordinary skill in the art, other mechanisms for achieving rotation relative to a longitudinal axis of the peg can also be used. Furthermore, there is preferably movement of the artificial eye in three dimensions, with rotation about the longitudinal axis of the peg ("the z axis") and movement along "x" and "y" axes of a plane perpendicular to the z axis.

For example, movement of the artificial eye relative to the peg has been achieved by a smooth convex peg surface that mates with a corresponding smooth concave surface on the posterior surface of an artificial eye; these convex and concave surfaces can interact to constitute a ball-and-socket articulation, i.e., a joint or coupling. A ball-and-socket peg embodiment permitted artificial eye movement in three dimensions. Movement of the artificial eye in three dimensions is preferred, since stresses or tension on the artificial eye were eliminated that would otherwise have caused the artificial eye to gap off of the underlying tissues at the extreme limits of gaze.

One embodiment of a ball-and-socket articulation comprises a socket that has an entry aperture that has a slightly smaller diameter than the diameter of the "ball" at the distal end of the peg. This embodiment is referred to as a "locking socket." The shape and volume of the socket accommodated the ball once the ball was pushed through the aperture. The "ball" had a lateral area that was held in place by the undermined areas of the "socket" adjacent the aperture, thereby creating the "locking" socket. The ball was generally removable from the socket by performing a reverse of the steps for insertion. Alternatively, a ball-and-socket articulation that has a locking socket configuration was prepared by using a barrel-shaped bit to drill the posterior surface of the artificial eye; once the bit had created an aperture and ground below the posterior surface of the artificial eye, the bit was rocked from side to side to undermine areas lateral to the aperture. In a further alternative, the locking socket was created by use of a second smaller bit that was inserted through the aperture created by a first bit; the smaller bit was then used to undermine the lateral areas.

A locking ball-and-socket embodiment is preferred as it permits movement of the artificial eye in three dimensions, and also provides support for the eye. The support provided by a locking socket can prevent an artificial eye from falling out of the orbit of a patient with shallow fornices, and serve to keep the peg or stint attached to the artificial eye at extremes of gaze.

One additional means of coupling the implant to the artificial eye is the use of magnets. For example, one pole of the magnet (for example, the "+" pole) is incorporated within a hydroxyapatite orbital implant. The opposite pole of the magnet (in this example, the "−" pole) is incorporated within the artificial eye. The attraction between poles causes the artificial eye to be coupled to the implant.

Vascularization Agents/ Therapeutic Methods

Relatedly, as indicated above, agents which promote vascularization may also be used in conjunction with orbital implants, particularly integrated orbital implants. Generally, the term "promote" with reference to vascularization denotes increasing the rate of blood vessel formation, or increasing the number of blood vessels per unit volume. Typically, the more that vascularization was promoted, the sooner the orbital implant was integrated into the patient's orbital socket. Even if integrated orbital implants are not used, improved vascularization in the area surrounding the implant may promote wound healing.

With self-tapping orbital implant pegs fewer procedures may be required to determine the vascularity of an integrated implant. For example, because the surface area of a self-tapping peg is smaller, concerns about potential infection may be less. Accordingly, procedures to assess peg vascularity, such as magnetic resonance imaging (MRI) or bone scan may not be needed.

One advantage of having the hydroxyapatite orbital implant impregnated with an agent that causes more rapid vascularization is that the patient can be fit with a prosthesis sooner, since the implant has vascularized more rapidly.

It is preferred that the motility peg should not be placed within the implant until there is good vascularization of the implant. Such vascularization took approximately six months in most patients and even longer in a small number of patients. Once the hydroxyapatite orbital implant was impregnated with fibrovascular tissue, the chances of implant migration were much decreased, as was the chance of it becoming infected.

Other porous implants, in addition to hydroxyapatite orbital implants, are also suitable, and may be vascularized. Preferably, the pores of the implant will be interconnected, i.e., the pores will not "dead end." This facilitates full vascularization.

Increase in vascularization may be accomplished by vascularization agents, such as growth factors. These growth factors may be applied via the orbital implant itself, for example, by dipping the orbital implant into a solution containing the vascularization agent prior to insertion of the orbital implant. Alternatively, as described above, the vascularization agent may be incorporated into the coating or wrapping material. For example, if a synthetic polymer is used, the polymer may be prepared such that the vascularization promoter is contained within the chains of the polymer molecules.. Another alternative is for the implant to be impregnated with a vascularization agent as part of the manufacturing process.

As yet another alternative, exogenous vascularizing agents may be applied as a post-operative therapy to encourage the integration of an integrated orbital implant or promote wound healing. One skilled in the art will envision other means for applying vascularization agents in this context to improve the rate or character of vascularization of the orbital implant.

Examples of agents which promote vascularization include growth factors, such as epidermal growth factor, fibroblast growth factor, neovascular growth factor, and epithelial growth factor. Also, serum or plasma, preferably from the patient himself to avoid antigenicity or disease transmission problems promotes vascularization. One skilled in the art will be able to ascertain other useful vascularization agents.

These agents which promote vascularization may also be used in conjunction with other agents which produce beneficial effects. For example, immunosuppressant or antibiotic agents may provide beneficial results and prevent undue immune response or insure against undue infection. Certain cell-adhesion modulating molecules, such as arginine-glycine-aspartic acid (RGD) containing compounds, or heparin may provide beneficial cell adhesion to the implant and thereby promote integration of integrated implants.

It should also be understood that vascularization agents may be contained in an impure medium or may be contained as a mixture of known ingredients. For example, it has been thought that dipping a hydroxyapatite integrated orbital implant into the patient's own normal human serum or plasma increases the rate and the degree of robustness of the vascularization. One skilled in the art will recognize that there are many vascularizing agents, some of which may also function as wound healing agents, or have other beneficial functions. The above list of vascularization agents is not intended to be complete, and it is not intended to provide limitation to the appended claims.

For example, in the practice of the therapeutic methods of the present invention, an effective amount of the active compound, including derivatives or salts thereof, or a pharmaceutical composition containing the same, is administered via any of the usual and acceptable methods known in the art, either singly or in combination with another compound or compounds of the present invention or other pharmaceutical agents such as immunosuppressants, antihistamines, corticosteroids, and the like.

Self-Tapping Implant Peg

There are several preferred embodiments for the self-tapping orbital implant peg. (See, e.g., FIGS. 1–5.) By use of high strength biocompatible implant materials such as commercially pure titanium, titanium alloys, stainless steel, CoCr alloys, tantalum or platinum, implant pegs can be fabricated which are capable of being inserted into an intact integrated implant in vivo.

The presently preferred material from which the self-tapping peg is fabricated is commercially pure titanium or a titanium alloy. These materials permit pegs to be manufactured which have the relevant size and strength needed to be a self-tapping peg for an integrated implant.

The self-tapping pegs generally contain a portion that can be placed beneath the conjunctiva covering the integrated implant, and a portion which protrudes from the implant when the peg is placed. The pegs of the invention have a diameter for the portion of the peg inserted into an integrated implant which is sufficiently small so as not cause undue or adverse trauma, i.e. produce minimal trauma, to the integrated implant during or after insertion. Examples of undue or adverse trauma include cracking the implant; crushing the porous implant, such that fibrovascular viability is impaired; providing a large surface area which provides a site for potential infection, and, damage to the integrated implant or surrounding tissues consequent to the torque applied to insert the peg, such as tearing loose the extraocular muscles from the integrated implant.

The strength of a preferred peg materials, such as cp—Ti and titanium alloys, permits pegs to be manufactured which are of smaller dimension than available polymeric pegs, while being strong enough to withstand the forces, e.g. torque, that are applied by the surgeon when the peg is inserted into the integrated implant.

Generally the self-tapping pegs comprise a threaded portion at a distal portion of the peg to facilitate insertion into the implant without the need for a pre-drilled hole. Threads 32 are depicted in FIG. 5. If desired, however, a surgeon may place a self-tapping peg in a predrilled hole. By use of pegs fabricated from materials such as commercially pure titanium (cp—Ti), self-tapping pegs are fabricated that are strong enough to be screwed into the implant without breaking. Non-threaded pegs having a "pin" configuration are also encompassed by the present invention. Threaded peg embodiments are presently preferred because they allow the surgeon to adjust the level of the self-tapping peg relative to the surface of the artificial eye, and the threads are believed to help prevent extrusion of the peg upon tissue growth in the integrated implant.

The preferred implant materials are particularly advantageous when used for threaded peg embodiments. A particularly advantageous property of a peg material is that the material can be manufactured with extremely sharp edges, e.g., a peg of this material can have extremely sharp threads. The "extreme sharpness is, e.g., a degree of sharpness that is not possible with pegs fabricated of polymeric material. It is believed that the sharper the peg threads, the easier it is for the surgeon to place the self-tapping peg into the integrated implant.

Generally the self-tapping pegs have a proximal region that facilitates the ability of the surgeon to hold or control the peg during insertion into the implant. This "control" region can comprise a slot capable of receiving a screwdriver tip, a receptacle capable of receiving a Phillips screwdriver tip, a polygonal surface capable of being held by a wrench, or a receptacle capable of being engaged by an Allen wrench; other means for controlling the peg will be apparent to one of ordinary skill in the art in view of the present disclosure, and are encompassed by the present invention.

Self-Tapping Sheath-Like Peg Embodiment

FIG. 3 depicts a sheath-like self-tapping peg embodiment placed in an integrated implant. Typically, the external surface of the sheath-like peg has threads to facilitate screwing into the integrated implant. The threads facilitate placement of the peg without the need for pre-drilling the implant.

Advantageously, a sheath-like self-tapping embodiment permits a smaller diameter of the portion of the peg that is screwed into the implant, while also permitting the lumen of the sheath to be dimensioned to hold a stint which is the same diameter as a stint fabricated of a material that requires pre-tapping, e.g., of 1.7 mm diameter because the materials from which the self-tapping pegs are constructed are stronger and permit thinner walls. This configuration is possible since the self-tapping peg is fabricated from a material such as titanium or its alloys.

Coupling of a Stint to an Artificial Eye

One embodiment for attaching an artificial eye to an implant is illustrated in FIG. 3. In this embodiment, a peg 20 in the shape of a closed ended sheath was placed into an integrated orbital implant 22. As illustrated, the peg protrudes from the surface of the implant a distance approximately equal to the thickness of the overlaying tissues. For the embodiment depicted in FIG. 3, the self-tapping peg was placed into the implant after sufficient time for fibrovascular ingrowth had occurred. The patient was then allowed to heal for a time sufficient to allow orbital tissue 30 (epithelial or fibrovascular) to grow between the peg and the walls of the hole. In the embodiments depicted in FIGS. 1, 3 and 4, the peg defines a cavity 24 as referenced in FIG. 3, into which orbital tissue 30 does not grow.

FIG. 3 depicts a cross-section of an integrated orbital implant after it has had a self-tapping peg placed therein. Preferred materials for a peg of the embodiment depicted in FIG. 3 are biocompatible and include polymers and metals.

Referring now to FIGS. 3 and 4, cavity 24 defined by peg 20 was capable of containing a stint 26 as shown in FIG. 4. An advantage of this peg embodiment is that human tissue is not regularly contacted during the insertion or removal of the stint from the sheath-like peg. By use of this embodiment, trauma to delicate orbital tissues was minimized or avoided, and patency of the peg lumen was maintained when the peg was removed. In other embodiments, during short-term removal of a peg the tissues lining the implant hole can swell, making peg reinsertion difficult; during longer-term peg removal, tissues can grow into and occlude the peg hole. Moreover, with a sheath-like embodiment, the surfaces regularly contacted during stint insertion and removal are not living tissue, and trauma to living tissue is avoided, as is any breakdown of the hydroxyapatite at the outer/upper margins of the implant adjacent the inserted self-tapping peg. Also the forces of the stint on the peg lumen are distributed by the peg. Forces of a peg placed in a drilled hole or of a rod-like self-tapping peg are transferred directly to the walls of the implant. Moreover, the stint can be readily changed, allowing for alternative means for attachment of the stint to the artificial eye to be utilized over time. Other advantages of a sheath-like peg include that it is more comfortable for the patient when the stint is inserted, relative, e.g., to screwing a self-tapping peg in and out or placing and removing a peg from a pre-tapped hole. Advantageously, the sheath-like peg can still be removed from the eye if necessary.

Stint 26 can be permanently attached to an artificial eye, or as appreciated by one of ordinary skill in the art can contain a mechanism at its distal end to provide for removable attachment to an artificial eye. For example, the distal end of the stint can comprise a smooth convex surface that mates with a corresponding smooth concave surface on the posterior surface of an artificial eye 28. In one embodiment, the distal end of the stint peg was essentially round in a cross-section perpendicular to a longitudinal axis of the peg, so that there was rotation of the artificial eye around a longitudinal axis of the stint. As appreciated by one of ordinary skill in the art, other mechanisms for achieving rotation relative to a longitudinal axis of the stint can also be used.

Furthermore, there was preferably movement of the artificial eye in three dimensions: with rotation about the longitudinal axis of the stint ("the z axis") and movement along "x" and "y" axes of a plane perpendicular to the z axis. For example, movement of the artificial eye relative to the stint has been achieved by a smooth convex stint surface that mates with a corresponding smooth concave surface on the posterior surface of an artificial eye; these convex and concave surfaces can interact to constitute a ball-and-socket articulation, such as illustrated in FIG. 2. A ball-and-socket embodiment has permitted artificial eye movement in three dimensions relative to the stint. As noted above, movement of the artificial eye in three dimensions is preferred.

One embodiment of a ball-and-socket articulation between an artificial eye and stint can comprise a socket that has an entry aperture that has a slightly smaller diameter than the diameter of the "ball" at the distal end of the stint. This embodiment is referred to as a "locking socket." The shape and volume of the socket accommodated the ball once the ball was pushed through the slightly smaller aperture. A ball-and-socket articulation that has such a socket configuration was prepared by using a barrel shaped bit to drill the posterior surface of the artificial eye; once the bit had created an aperture and had ground below the posterior surface, the bit was rocked from side to side to undermine areas lateral to the aperture, or a second smaller bit was inserted through the aperture and the smaller bit was used to undermine the lateral areas.

Self-Tapping Rod-Like Peg Embodiment

FIG. 5 depicts a rod-like peg embodiment placed in an integrated implant. Typically, the external surface of the peg has threads 32 to facilitate screwing into the integrated implant. The threads facilitate placement of the peg without the need for pre-drilling the implant. Threaded peg embodiments are preferred because they allow the physician to adjust the level of the self-tapping peg relative to the surface of the artificial eye, and the threads are believed to help prevent extrusion of the peg upon tissue ingrowth.

Peg Placement

Accordingly, after coating the peg, such as that of FIG. 3, with antibiotic the threaded peg was screwed to a level approximately 2–3 mm beneath the surface of the conjunctiva. A temporary stint was placed in the cavity of the peg. After healing was allowed for approximately four weeks, the temporary stint was replaced with a ball headed stint, where the ball of the stint was capable of mating with a complementary recess on the posterior surface of an artificial eye, to create a ball-and-socket joint when the artificial eye was in place.

In the embodiment depicted in FIG. 4, the artificial eye 28 is coupled to a sheath-like embodiment of peg 20 by a stint 26. The stint was configured to fit in the cavity 24 defined by the peg, depicted in FIG. 3. Preferably, the distal end of the stint permitted rotation of the artificial eye around a longitudinal axis of the stint, and more preferably permitted movement in three dimensions relative to a pivot point generally located on the longitudinal axis of the stint. Accordingly, a smooth convex surface such as a ball was formed on the distal end of the stint; the convex surface mated with a corresponding concave indentation on the posterior surface of the prothesis to create a "ball-and-socket" coupling. As disclosed herein, a "locking" ball-and-socket is particularly preferred.

EXAMPLES

Examples

Present sheath-like polymeric implant pegs (Integrated Orbital Implants, San Diego, Calif.) are approximately 11 mm long, 4 mm in diameter, and have a lumen diameter of 2 mm; the stint which fits into the lumen is approximately 1.7 mm in diameter. This peg has threads on the external surface, the threads are as sharp as possible for a peg of these dimensions fabricated from a typical polymeric material such as polyethylene.

A self-tapping sheath-like peg is approximately 13 mm long, 2.8 mm in diameter, with a lumen of approximately 1.2 mm; the stint which fits into the lumen is approximately 1 mm in diameter. The stint is made from cp—Ti or a biocompatible titanium alloy. The external surface of the peg is threaded, so as to provide the ability to place the peg without the need for drilling a hole. These threads are particularly sharp, sharper than possible with threads on present polymeric (e.g., polyethylene) pegs of approximately 4 mm diameter. Care should be exercised by anyone when handling the self-tapping peg, as the threads could injure the person's skin or could penetrate surgical gloves.

A stint for the self-tapping peg is fabricated from the preferred materials cp—Ti or biocompatible titanium alloy. The stint is approximately 1 mm in diameter. Preferably, the stint has, circumferential indentations at periodic distances, e.g., every 3 mm, along the length of the stint. The circumferential indentations permit the surgeon to readily modify the length of the stint without use of any cutting tool, or to facilitate cutting with a tool. Advantageously, one end of the stint has a spherical head. The ocularist can create a receptacle on the posterior surface of the artificial eye that mates with the spherical head. Most preferably, the ocularist creates a locking socket on the posterior surface of the eye.

Alternatively, the stint is fabricated from a material that retains shape after it is bent. One example of a material that provides such an amended shape following bending is stainless steel; other material that provide for an amended shape following bending are well known to those of ordinary skill in the art. This embodiment is used to advantage if the peg has been inserted into the implant at an angle other than perpendicular to a frontal plane at the surface of the implant.

Closing

It must be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar to equivalent to those described herein can be used in the practice or testing of the invention, the preferred methods and materials are now described. All publications or documents mentioned herein are fully incorporated by reference herein.

What is claimed is:

1. An orbital prosthesis comprises:

an orbital implant;

a self-tapping hollow peg being insertable into said implant and defining an inner peg cavity; and a stint having a portion sized to reside in said cavity;

wherein said stint further comprises:

circumferential indentations regularly spaced along a longitudinal axis thereof, whereby a length of the stint can be shortened by breaking at any one of the circumferential indentations by bending the stint.

2. The stint of claim 1, wherein the circumferential indentations are regularly spaced at about every 3 mm.

3. A stint comprising an oblong portion shaped and dimensioned to reside within a cavity formed in an orbital prosthesis, wherein said portion comprises at least a first indentation, whereby a length of said stint is shortenable by breaking the stint at said first indentation.

4. The stint of claim 3, wherein said indentation is circumferential about a major axis of said portion.

5. The stint of claim 3, which further comprises a second indentation.

6. The stint of claim 5, wherein said first and second indentations are spaced apart by about 3 millimeters.

7. The stint of claim 3, wherein said stint further comprises means for removable attachment to an artificial eye.

8. The stint of claim 7, wherein said means for removable attachment comprises a convex surface sized and shaped to articulate with a concave surface on said artificial eye.

9. The stint of claim 7, wherein said means for removable attachment comprises a ball or socket of a ball-and-socket articulation.

10. The stint of claim 3, wherein said stint further comprises means for permanent attachment to an artificial eye.

11. The stint of claim 3, wherein said portion is substantially cylindrical having a diameter of about 1.7 millimeters.

* * * * *